US010196525B2

(12) United States Patent
Oota et al.

(10) Patent No.: US 10,196,525 B2
(45) Date of Patent: Feb. 5, 2019

(54) PRODUCTION METHOD FOR BASIC ZINC CYANURATE POWDER AND PRODUCTION METHOD FOR RUST-PREVENTIVE PIGMENT COMPOSITION

(71) Applicant: NISSAN CHEMICAL INDUSTRIES, LTD., Tokyo (JP)

(72) Inventors: Isao Oota, Sodegaura (JP); Shigeo Hattori, Toyama (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 107 days.

(21) Appl. No.: 15/323,148

(22) PCT Filed: Jul. 6, 2015

(86) PCT No.: PCT/JP2015/069468
§ 371 (c)(1),
(2) Date: Dec. 30, 2016

(87) PCT Pub. No.: WO2016/006585
PCT Pub. Date: Jan. 14, 2016

(65) Prior Publication Data
US 2017/0130062 A1 May 11, 2017

(30) Foreign Application Priority Data

Jul. 9, 2014 (JP) .................................. 2014-141756
Sep. 4, 2014 (JP) .................................. 2014-180394

(51) Int. Cl.
*C09D 5/08* (2006.01)
*C09D 7/40* (2018.01)
(Continued)

(52) U.S. Cl.
CPC ............ *C09D 5/086* (2013.01); *C07D 251/32* (2013.01); *C09C 1/04* (2013.01); *C09C 3/08* (2013.01);
(Continued)

(58) Field of Classification Search
CPC . C09D 5/086; C09D 7/40; C09D 7/69; C09D 7/68; C09D 7/70; C09D 167/08;
(Continued)

(56) References Cited

U.S. PATENT DOCUMENTS 4,329,381 A * 5/1982 Eschwey .............. C07D 277/72
106/14.37
4,507,270 A * 3/1985 Harth .................... C07D 251/32
423/365
2013/0108871 A1 5/2013 Oota et al.

FOREIGN PATENT DOCUMENTS

CN 102391196 A 3/2012
JP S59-31779 A 2/1984
(Continued)

OTHER PUBLICATIONS

Oct. 6, 2015 Search Report issued in International Patent Application No. PCT/JP2015/069468.

*Primary Examiner* — Peter F Godenschwager
*Assistant Examiner* — Andrew J. Oyer
(74) *Attorney, Agent, or Firm* — Oliff PLC

(57) ABSTRACT

A method produces a basic zinc cyanurate powder, the amount of a portion thereof which remains in a sieve having a mesh size of 1,000 μm being less than 1 mass %. The method includes heating, at 30 to 300° C., a powder-form mixture which is composed of zinc oxide, cyanuric acid, and water, which has a ratio by mole of zinc oxide to cyanuric acid of 2 to 3, and which has a water content of 9 to 18 mass %, in a closed or unclosed state.

15 Claims, 5 Drawing Sheets

(51) Int. Cl.
  *C09D 167/08* (2006.01)
  *C09D 201/00* (2006.01)
  *C09C 3/08* (2006.01)
  *C07D 251/32* (2006.01)
  *C09C 1/04* (2006.01)
  *C08K 5/3492* (2006.01)

(52) U.S. Cl.
  CPC ............... *C09D 7/40* (2018.01); *C09D 7/68* (2018.01); *C09D 7/69* (2018.01); *C09D 7/70* (2018.01); *C09D 167/08* (2013.01); *C09D 201/00* (2013.01); *C08K 5/34928* (2013.01); *C08K 2201/005* (2013.01)

(58) Field of Classification Search
  CPC ...... C09D 201/00; C09D 3/08; C09D 251/32; C09D 1/04; C08K 5/34928; C08K 2201/005
  See application file for complete search history.

(56) References Cited

FOREIGN PATENT DOCUMENTS

| | | |
|---|---|---|
| JP | S62-5194 B2 | 2/1987 |
| WO | 2011/162353 A1 | 12/2011 |

\* cited by examiner

PRODUCTION METHOD FOR BASIC ZINC CYANURATE POWDER AND PRODUCTION METHOD FOR RUST-PREVENTIVE PIGMENT COMPOSITION

TECHNICAL FIELD

The present invention relates to a method for producing a basic zinc cyanurate powder, and to a method for producing a rust-preventive pigment composition using the basic zinc cyanurate powder.

BACKGROUND ART

Rust-preventive pigments used as a steel structure coating paint, a mirror back-coating paint, etc. must be free from lead and chromium, according to the RoHS directive (Directive on the Restriction of the Use of Certain Hazardous Substances in Electrical and Electronic Equipment) and the WEEE directive (Directives on Waste Electrical and Electronic Equipment, directed to collection of equipment and recycle rate), which were put into effect in the European Union in 2006. Specifically, electrical and electronic equipment containing any of six designated hazardous substances (lead, mercury, cadmium, hexavalent chromium, polybromobiphenyl, and poly(bromodiphenyl ether)) in an amount greater than an allowed level cannot be sold. Among the designated hazardous substances, limitations are imposed on the allowable levels of hexavalent chromium and lead to 1,000 ppm or lower.

In Japan, the Ministry of Economy, Trade and Industry has expressed that "it is appropriate for any company to disclose information about environmentally hazardous substances; i.e., the six substances regulated by the RoHS directive, contained in their products." Thus, such an action on the RoHS directive must be also taken in Japan, and other commercial products will be targeted in addition to electric and electronic equipment. Also, in Japan, the "Act on Confirmation, etc. of Release Amounts of Specific Chemical Substances in the Environment and Promotion of Improvements to the Management Thereof" (the regulation of Pollutant Release and Transfer Register (abbreviated as PRTR)) was enacted in 1999, and 354 chemical substances were designated. Some chromium compounds and lead compounds are designated substances.

In Japan, according to the JIS standards, rust-preventive coatings containing a rust-preventive pigment such as a chromium compound or a lead compound (e.g., red lead, basic lead chromate, zinc chromate, basic zinc potassium chromate, lead cyanamide, calcium plumbate, and basic lead sulfate) have been invalid since fiscal year 2014. Therefore, there is keen demand for an inexpensive, Pb-free, and Cr-free rust-preventive pigment exhibiting excellent anti-corrosive property.

Examples of currently employed Pb-free and Cr-free rust-preventive pigments include zinc salts such as zinc phosphate, zinc phosphite, and zinc molybdate; aluminum salts such as aluminum phosphate and aluminum molybdate; calcium salts such as calcium phosphate and calcium molybdate; and cyanamide compounds such as zinc cyanamide and zinc calcium cyanamide.

Other than the above zinc salts, a zinc salt cyanuric acid is disclosed as a component of a metal-surface anti-corrosive coating containing conventional ingredients and an organic zinc salt. A zinc cyanurate production method is also disclosed. In the method, zinc oxide is reacted with cyanuric acid in boiling water advantageously in the presence of a small amount of acetic acid serving as a catalyst, whereby a zinc cyanurate of interest is formed (see Patent Document 1).

Another production method is disclosed. In the method, zinc oxide and cyanuric acid are mixed together with water in a possible small amount of 10 to 80 mass % (with respect to paste), so as to prepare a kneadable paste, and shear force is applied to the prepared paste while the mixture is heated at 50 to 250° C., to thereby produce basic zinc cyanurate (see Patent Document 2). More specifically, in the Examples of Patent Document 2, desalted water, zinc oxide, and cyanuric acid are mixed by means of a paddle dryer equipped with a blade mill, to thereby prepare a paste having a water content of 70 mass %. The paste is heated at 105 to 110° C. and then dried under reduced pressure, whereby basic zinc cyanurate is yielded. The reaction is performed in a paste form, requiring post drying.

In still another disclosed production method, at least one selected from zinc oxide and basic zinc oxide is mixed with cyanuric acid and water such that the cyanuric acid concentration with respect to water is adjusted to 0.1 to 10.0 mass %, to thereby prepare a slurry. The slurry is wet-dispersed at 5 to 55° C. by the mediation of a dispersion medium, to thereby produce basic zinc cyanurate (see Patent Document 3).

In these basic zinc cyanurate production methods, reaction is performed in a slurry or paste state containing water and basic zinc cyanurate particles. Accordingly, for employing the thus-produced basic zinc cyanurate as a rust-preventive pigment, the obtained slurry or paste must be dried and pulverized under dry conditions to yield a micropowder. However, such a slurry or paste contains a large amount of water, and drying cost increases. Also, the dried product assumes a lumpy form with very high hardness. Thus, forming micropowder requires a very large amount of energy, increasing pulverization cost, which is disadvantageous.

Meanwhile, a rust-preventive coating paint or a corrosion-inhibiting coating agent for iron and the like employing zinc cyanurate as a rust-preventive pigment is disclosed. The disclosed undercoating paint for baking finish is based on an epoxy resin ester and is formed of a varnish (1373.5 parts by mass) and zinc cyanurate (Zn: 31.7%) (26.5 parts by mass) serving as a corrosion-inhibitor, wherein the varnish has the following composition: epoxy resin-castor oil fatty acid ester (fatty acid content: 42%, 60% in xylol) (400 parts by mass), zinc phosphate (110 parts by mass), microtalc (120 parts by mass), titanium dioxide (rutile) (80 parts by mass), barite (193.5 parts by mass), ethylene glycol (15 parts by mass), n-butanol (15 parts by mass), tetralin (30 parts by mass), a higher aromatic compound (110 parts by mass), a non-plasticized urea resin (65% in butanol) (110 parts by mass), and xylol (200 parts by mass) (see Patent Document 1).

PRIOR ART DOCUMENTS

Patent Documents

Patent Document 1: Japanese Patent Publication (kokoku) No. 1987-5194
Patent Document 2: U.S. Pat. No. 4,507,270
Patent Document 3: Re-publication of PCT International Publication No. 2011/162353, pamphlet

SUMMARY OF THE INVENTION

Problems to be Solved by the Invention

An object of the present invention for solving the aforementioned problems involved in conventional techniques is to provide a low-cost method for efficiently producing powder-form basic zinc cyanurate without performing a pulverization step through a reaction via no state of slurry or paste. Another object is to provide a method for producing a rust-preventive pigment composition by use of the basic zinc cyanurate powder produced according to the present invention.

Means for Solving the Problem

The present inventors conducted extensive studies in order to attain the above objects, and have found a method for efficiently producing a basic zinc cyanurate powder, the amount of a portion thereof which remains in a sieve having a mesh size of 1,000 μm (hereinafter may be referred to as a 1,000 μm-sieve remaining amount, and similar expression will be applied throughout the specification) being less than 1 mass %, characterized in that the method comprises heating, at 30 to 300° C., a powder-form mixture which is composed of zinc oxide, cyanuric acid, and water, which has a ratio by mole of zinc oxide to cyanuric acid of 2 to 3, and which has a water content of 9 to 18 mass %, in a closed or unclosed state.

Accordingly, in a first mode of the present invention, there is provided a method for producing a basic zinc cyanurate powder, the amount of a portion thereof which remains in a sieve having a mesh size of 1,000 μm being less than 1 mass %, characterized in that the method comprises heating, at 30 to 300° C., a powder-form mixture which is composed of zinc oxide, cyanuric acid, and water, which has a ratio by mole of zinc oxide to cyanuric acid of 2 to 3, and which has a water content of 9 to 18 mass %, in a closed or unclosed state.

A second mode is directed to a specific embodiment of the method of the first mode for producing a basic zinc cyanurate powder, the amount of a portion thereof which remains in a sieve having a mesh size of 1,000 μm being less than 1 mass %, wherein the powder-form mixture has a 1,000 μm-sieve remaining amount less than 1 mass % and a 400 μm-sieve remaining amount less than 10 mass %.

A third mode is directed to a specific embodiment of the method of the first or second mode for producing a basic zinc cyanurate powder, the amount of a portion thereof which remains in a sieve having a mesh size of 1,000 μm being less than 1 mass %, wherein the basic zinc cyanurate powder has a primary particle longer axis of 50 to 2,000 nm and a primary particle shorter axis of 20 to 300 nm, as obtained through observation of the primary particles under a transmission electron microscope.

A fourth mode is directed to a specific embodiment of the method of the third mode for producing a basic zinc cyanurate powder, the amount of a portion thereof which remains in a sieve having a mesh size of 1,000 μm being less than 1 mass %, wherein the ratio of the longer axis of the zinc cyanurate particle to the shorter axis thereof is 2 to 10.

A fifth mode is directed to a specific embodiment of the method of any one of the first to fourth modes for producing a basic zinc cyanurate powder, the amount of a portion thereof which remains in a sieve having a mesh size of 1,000 μm being less than 1 mass %, wherein heating is performed by means of a powder mixer having mixing means and heating means.

In a sixth mode, there is provided a method for producing a rust-preventive pigment composition, the method comprising the following steps (a) and (b):

step (a): a step of forming a basic zinc cyanurate powder, the amount of a portion thereof which remains in a sieve having a mesh size of 1,000 μm being less than 1 mass %, by heating, at 50 to 300° C., a powder-form mixture which is composed of zinc oxide, cyanuric acid, and water, which has a ratio by mole of zinc oxide to cyanuric acid of 2 to 3, and which has a water content of 9 to 18 mass %, in a closed or unclosed state; and step (b): a step of mixing the zinc cyanurate powder produced in step (a), the amount of a portion thereof which remains in a sieve having a mesh size of 1,000 μm being less than 1 mass %, with a binder component and a diluent.

A seventh mode is directed to a specific embodiment of the method of the sixth mode for producing a rust-preventive pigment composition, wherein the binder is an oily binder or a synthetic resin binder.

An eighth mode is directed to a specific embodiment of the method of the sixth mode for producing a rust-preventive pigment composition, wherein the diluent is at least one species selected from the group consisting of water, turpentine, mineral spirit, toluene, xylene, methyl ethyl ketone, methyl isobutyl ketone, cellosolve acetate, ethanol, butanol, isopropyl alcohol, cyclohexane, ethyl acetate, and butyl acetate.

Effects of the Invention

The powder of basic zinc cyanurate particles produced according to the present invention, the amount of a portion thereof which remains in a sieve having a mesh size of 1,000 μm being less than 1 mass %, can be used as a non-hazardous (Pb- and Cr-free) rust-preventive pigment exhibiting excellent rust prevention performance. In addition, the thus-obtained basic zinc cyanurate powder is white in appearance. Thus, when the basic zinc cyanurate powder is used in a rust-preventive pigment composition, other coloring pigments are not substantially affected by the basic zinc cyanurate powder. As a result, rust-preventive pigment compositions having various colors can be prepared.

MODES FOR CARRYING OUT THE INVENTION

Figure 1:
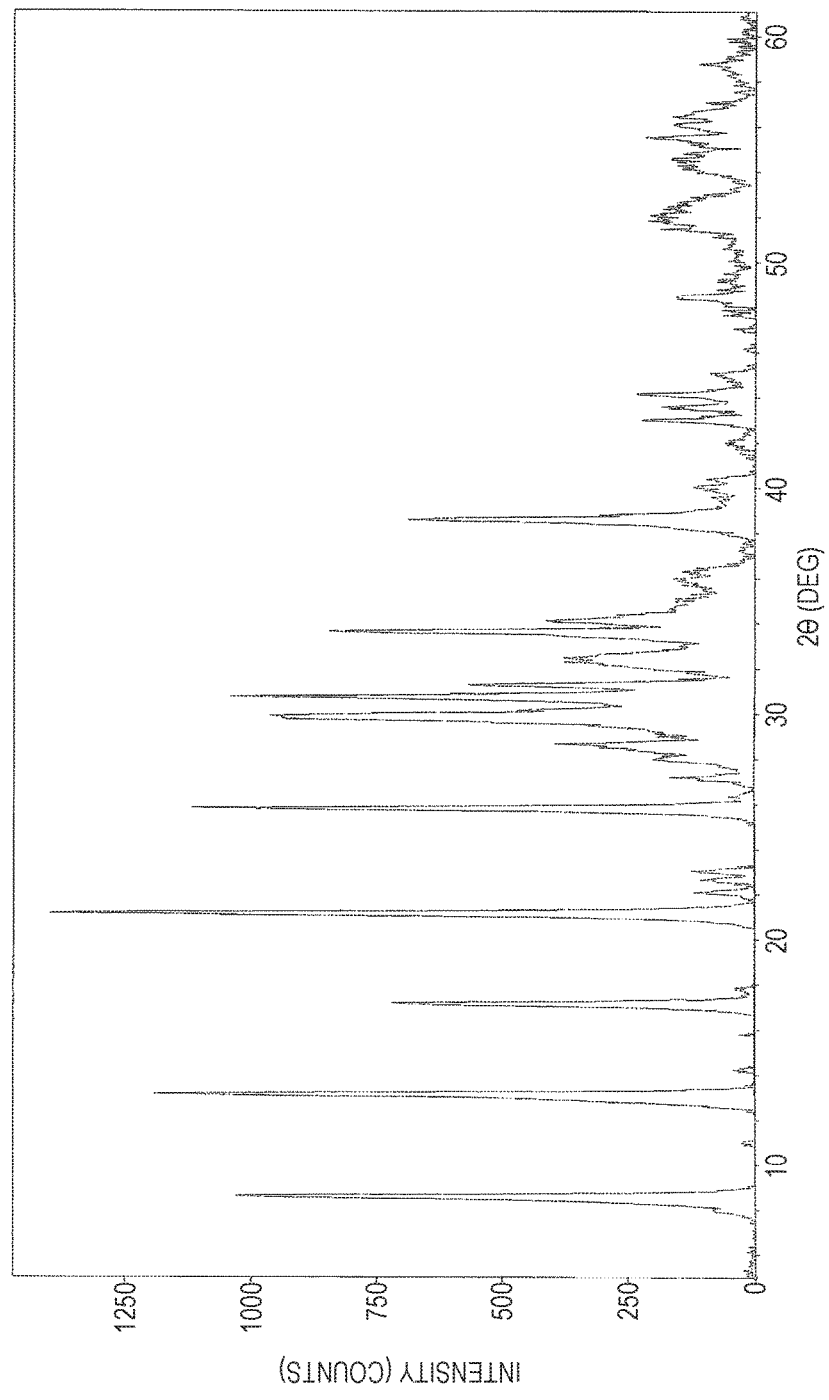
FIG. 1 An XRD pattern of Example 1
Figure 2:
FIG. 2 A transmission electron microscope photoimage of Example 1
Figure 3:
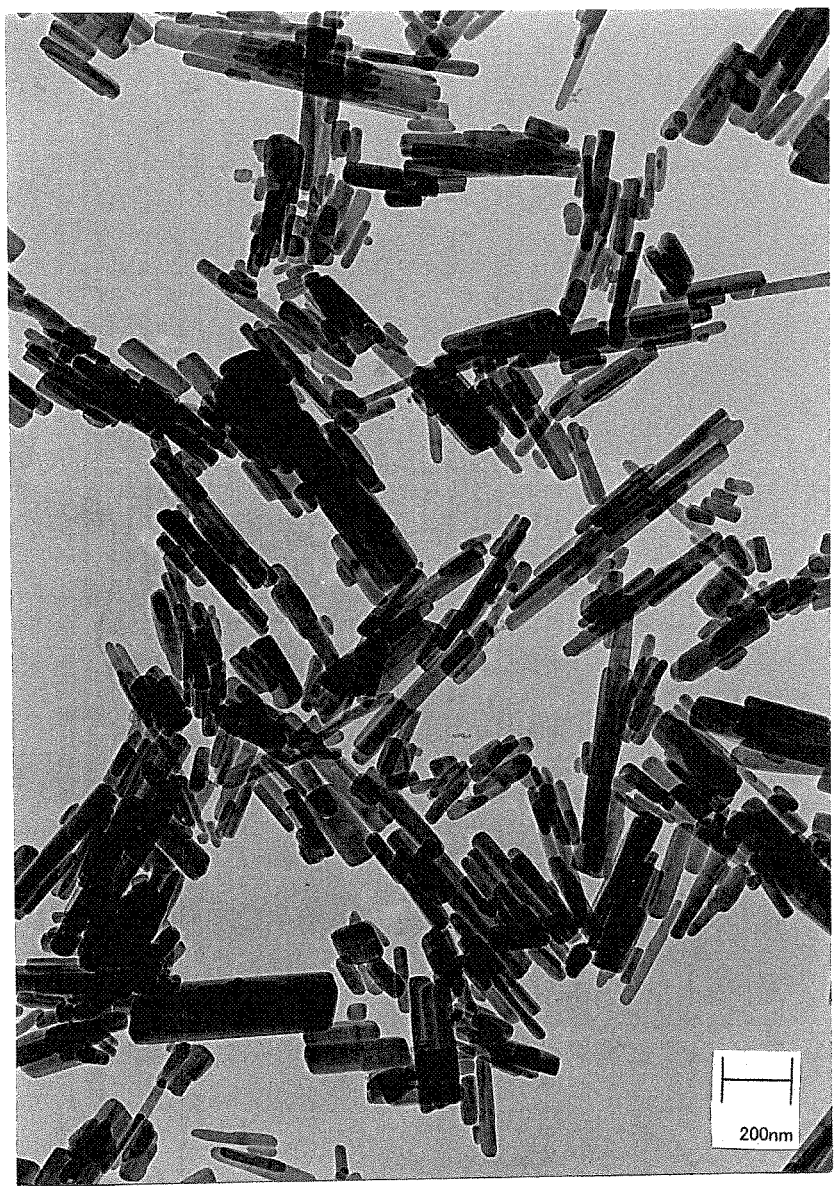
FIG. 3 A transmission electron microscope photoimage of Example 2
Figure 4:
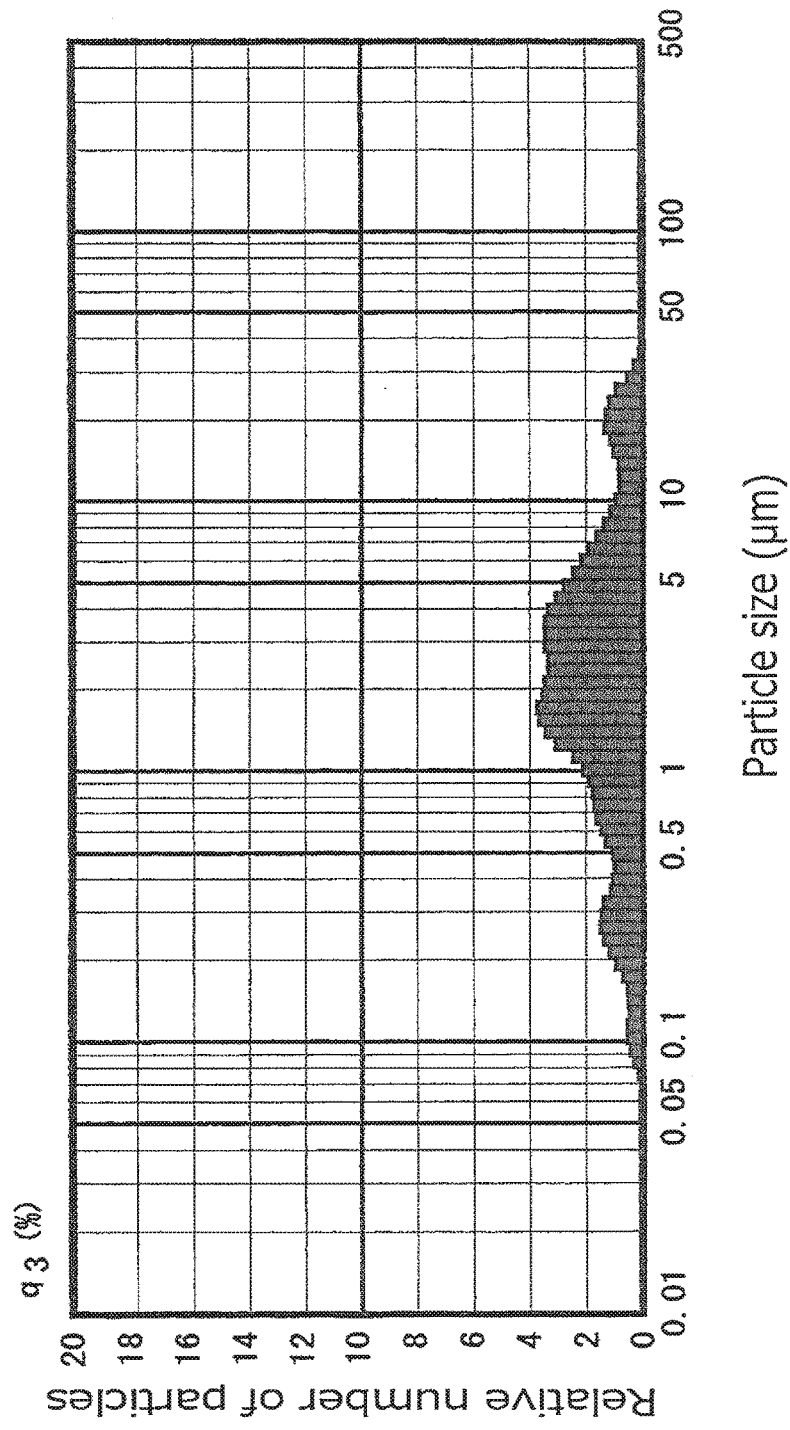
FIG. 4 A chart of particle size measurement by laser technique (Example 12)
Figure 5:
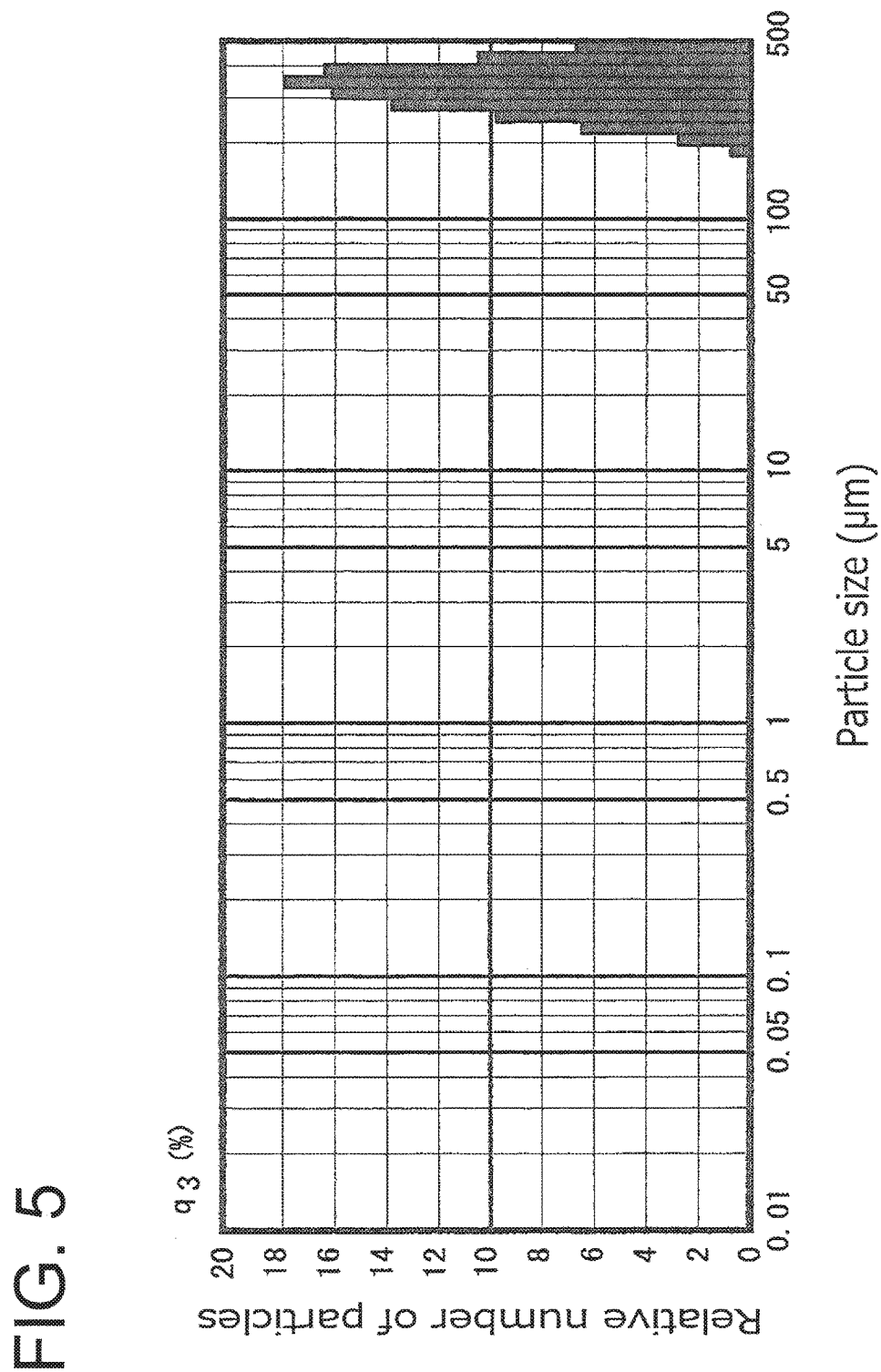
FIG. 5 A chart of particle size measurement by laser technique (Comparative Example 5)

The present invention is directed to a method for producing a zinc cyanurate powder, the amount of a portion thereof which remains in a sieve having a mesh size of 1,000 μm being less than 1 mass %, characterized in that the method comprises heating, at 30 to 300° C., a powder-form mixture which is composed of zinc oxide, cyanuric acid, and water, which has a ratio by mole of zinc oxide to cyanuric acid of 2 to 3, and which has a water content of 9 to 18 mass %, in a closed or unclosed state.

In the present invention, zinc oxide powder commercial products of any of grades 1, 2, and 3 may be used. As cyanuric acid, cyanuric acid powder (product of Nissan Chemical Industries, Ltd.) may be used.

In the present invention, the powder-form mixture which is composed of zinc oxide, cyanuric acid, and water, which has a ratio by mole of zinc oxide to cyanuric acid of 2 to 3, and which has a water content of 9 to 18 mass % preferably has a particle size distribution profile including 1,000 μm-sieve remaining amount less than 1 mass % and a 400 μm-sieve remaining amount less than 10 mass %. To attain these conditions, zinc oxide and cyanuric acid serving as raw materials each preferably have a particle size distribution profile including 1,000 μm-sieve remaining amount less than 1 mass % and a 400 μm-sieve remaining amount less than 10 mass %. In the present invention, the sieve remaining amount may be determined by placing a sample into a stainless steel sieve having a mesh size (inner opening diameter) of 200 mm, and the sieve is subjected to shaking by means of a Ro-Tap shaker. Then, the mass of the sample remaining in the sieve is measured, to thereby determine the sieve remaining amount.

In the present invention, the ratio by mole of zinc oxide to cyanuric acid is 2 to 3, preferably 2.5. When the ratio by mole of zinc oxide to cyanuric acid in the powder-form mixture is greater than 3, a large amount of zinc oxide remains after reaction, whereas the mole ratio is smaller than 2, a large amount of cyanuric acid remains after reaction. Needless to say, both cases are not preferred. For forming a single phase of basic zinc cyanurate, the ratio by mole of zinc oxide to cyanuric acid in the powder-form mixture is preferably 2.5.

In the present invention, the powder-form mixture which is composed of zinc oxide, cyanuric acid, and water has a water content of 9 to 18 mass %. When the water content is smaller than 8%, unreacted zinc oxide and cyanuric acid disadvantageously remain, whereas when the powder-form mixture has a water content in excess of 18 mass % and to 80 mass %, the mixture does not assume a powder form, but a wet cake or a paste. In this case, the mixture fails to pass through a sieve having a mesh size of 1,000 μm, and therefore, the sieve remaining amount is 100 mass %. When the water content is in excess of 80 mass %, the mixture assumes a high-viscosity slurry. When such a mixture is heated at 30 to 300° C., a hard cake or a high-viscosity paste is obtained. In order to form a powder thereof, drying and dry-pulverization are further required. Thus, the production efficiency is poor, thereby failing to provide a low-cost production method. The water content is preferably 11 to 15 mass %.

In the present invention, the aforementioned powder-form mixture may be prepared through any method selected from the following methods: a technique in which zinc oxide, cyanuric acid, and water are simultaneously mixed together; a technique in which zinc oxide and cyanuric acid are preliminarily mixed, and water is added to the mixture, followed by mixing; a technique in which zinc oxide and water are preliminarily mixed, and cyanuric acid is added to the mixture, followed by mixing; and a technique in which cyanuric acid and water are preliminarily mixed, and zinc oxide is added to the mixture, followed by mixing.

In the present invention, heating is performed at 30 to 300° C. in a closed or unclosed state. When the heating temperature is lower than 30° C., reaction is considerably retarded, whereby large amounts of unreacted zinc oxide and powder-form cyanuric acid remain, which is not preferred. Also, although the heating treatment may be performed at 300° C., an expensive high-pressure apparatus is required when the heating temperature is in excess of 100° C. Thus, in order to produce a basic zinc cyanurate powder at lower cost, heating is preferably performed at 50 to 100° C., at which no particular high-pressure apparatus is employed.

In the present invention, heating is preferably performed by means of a powder mixer having mixing means and heating means in the case of production in a large industrial scale. Specific examples of the powder mixer include a Henschel mixer, a Loedige mixer, a Nauta mixer, and a rotary kiln, which are heating reaction containers enabling stirring/mixing in a closed or unclosed manner.

The basic zinc cyanurate produced according to the present invention has a 1,000 μm-sieve remaining amount less than 1 mass %. Preferably, the basic zinc cyanurate produced according to the present invention has a 400 μm-sieve remaining amount less than 10 mass %.

Furthermore, the basic zinc cyanurate produced according to the present invention preferably has a primary particle longer axis of 50 to 2,000 nm and a primary particle shorter axis of 20 to 300 nm, as obtained through observation of the primary particles under a transmission electron microscope. More preferably, the ratio of the longer axis of the zinc cyanurate particle to the shorter axis thereof is 2 to 10.

The basic zinc cyanurate produced according to the present invention exhibits the same powder X-ray diffraction pattern as that of the basic zinc cyanurate produced in Example 1 of WO 2011/162353. The basic zinc cyanurate is identified as a compound represented by formula $Zn_5(C_3N_3O_3)_2(OH)_3 \cdot 3H_2O$.

Also, the basic zinc cyanurate powder produced according to the present invention has a negative surface charge in an aqueous medium having a pH of 3 to 10. Thus, the powder obtained in the invention exhibits an excellent dispersibility in an aqueous medium from an acidic pH region to an alkaline pH region and an excellent compatibility to a synthetic resin or an emulsion thereof for preparing a water-base rust-preventing coating. Thus, a stable water-base rust-preventing coating can be successfully produced.

The rust-preventive pigment composition production method according to the present invention including the following steps (a) and (b):

step (a): a step of forming a basic zinc cyanurate powder, the amount of a portion thereof which remains in a sieve having a mesh size of 1,000 μm being less than 1 mass %, by heating, at 50 to 300° C., a powder-form mixture which is composed of zinc oxide, cyanuric acid, and water, which has a ratio by mole of zinc oxide to cyanuric acid of 2 to 3, and which has a water content of 9 to 18 mass %, in a closed or unclosed state; and step (b): a step of mixing the zinc cyanurate powder produced in step (a), the amount of a portion thereof which remains in a sieve having a mesh size of 1,000 μm being less than 1 mass %, with a binder component and a diluent.

In step (b), examples of the binder include an oily binder or a synthetic resin binder. Examples of the oily binder include boiled oil, linseed oil, soy bean oil, safflower oil, and castor oil. Examples of the synthetic resin binder include phthalic resin, acrylic resin, amino resin, epoxy resin, silicone resin, polyurethane resin, fluororesin, and vinyl chloride resin.

Examples of the diluent include water, and organic solvents such as turpentine, mineral spirit, toluene, xylene, methyl ethyl ketone, methyl isobutyl ketone, cellosolve acetate, ethanol, butanol, isopropyl alcohol, cyclohexane, ethyl acetate, and butyl acetate.

In the rust-preventive pigment composition production method of the present invention, the mixing proportions of the zinc cyanurate powder having a 1,000 µm-sieve remaining amount less than 1 mass %, the binder, and the diluent may be adjusted to any values. In one case, a composition composed of a zinc cyanurate powder having a 1,000 µm-sieve remaining amount less than 1 mass % (30 to 80 parts by mass), a binder (5 to 20 parts by mass), and a diluent (2 to 50 parts by mass) can provide a rust-preventive pigment composition having excellent rust prevention performance. The thus-produced rust-preventive pigment composition assumes a viscous slurry.

The rust-preventive pigment composition produced according to the present invention is a non-hazardous rust-preventive pigment composition which exhibits a rust prevention effect equivalent to or higher than that of a rust-preventive pigment composition containing a hazardous substance such as red lead or lead cyanamide. The rust-preventive pigment composition, which contains no hazardous substance; i.e., lead or chromium, can serve as a non-hazardous rust-preventive pigment composition incorporated into a rust-preventive coating applicable to a station house, where people often touch parts thereof, a road guardrail, etc.

The basic zinc cyanurate powder produced according to the present invention is white. Thus, by mixing a coloring pigment, the rust-preventive pigment composition produced according to the present invention may be transformed into a rust-preventive pigment composition of a color of interest.

The rust-preventive pigment composition produced according to the present invention may be applied to a target object through a conventionally known technique (e.g., by means of a brush, a roller, or a spray gun).

Differing from a heavy duty (long-term) rust-preventive composition such as a zinc-rich paint, the rust-preventive pigment composition produced according to the present invention serves as a rust-preventive pigment composition for providing an object with short-term durability. Thus, the composition is suited for a case where the composition is renewed by painting after heavy staining at a cycle of 5 to 10 years (e.g., the aforementioned station house, road guardrail, etc.).

EXAMPLES

Hereinafter, the present invention will be described in more detail by way of the Synthetic Examples, Examples, Comparative Examples, and Referential Examples. However, the Examples should not be construed as limiting the invention thereto.

(Measurement Apparatuses)

Analyses in the Examples and the Comparative Examples were performed by means of the following apparatuses under the following conditions.

1) Transmission electron microscopic observation: Observed under JEM-1010 (product of JEOL Ltd., acceleration voltage: 100 kV)

2) Laser diffraction particle size determination: Determined by means of SALD-7000 (product of Shimadzu Corporation). A 0.04 mass % aqueous dispersion was used as a measurement sample.

3) Particle size distribution of powder: Stainless steel sieves (mesh sizes: 1,000 µm, 400 µm, 160 µm, 75 µm, and 45 µm) were stacked from top to bottom. A sample was sieved by means of a Ro-Tap shaker, and the sieve remaining amount was measured for each sieve.

4) Specific surface area: Determined by means of a nitrogen adsorption surface area measurement device Monosorb (product of Quantachrome). A sample was dried at 200° C. before measurement.

5) Water content of powder: A sample (about 2 g) was placed in a ceramic crucible, and the mass of the sample was precisely measured. The sample was then dried at 110° C., and the mass was measured again. From the two measurements, the water content of the sample (mass %) was calculated.

6) Powder X-ray diffraction analysis: Performed by means of a powder X-ray diffractometer RINT Ultima (product of Rigaku Corporation)

7) Viscosity: Determined by means of a B-type viscometer (product of Tokyo Keiki Inc.).

8) Zeta potential: Determined by means of a laser zeta potentiometer ELS-6000 (product of Otsuka Electronics Co., Ltd.).

Example 1

Zinc oxide powder (480 g) having a given particle size (i.e., a 45 µm-sieve remaining amount of 0.01 mass % or less) (grade 2 zinc oxide, product of Sakai Chemical Industry Co., Ltd.) and cyanuric acid powder (320 g) having a given particle size (i.e., a 400 µm-sieve remaining amount of 0 mass %, a 160 µm-sieve remaining amount of 1.1 mass %, and a 45 µm-sieve remaining amount of 82.6 mass %) (product of Nissan Chemical Industries, Ltd., water content: 5.1 mass %) were placed in a polyethylene container (capacity: 3 L), and then pure water (101 g) was added to the container. The container was placed on a shaker, and the contents were mixed for 10 minutes. Through the procedure, 901 g of a raw material powder having a zinc oxide/cyanuric acid mole ratio of 2.5 and a water content of 13 mass % was prepared. The raw material powder was found to have a 1,000 µm-sieve remaining amount of 0 mass %, a 400 µm-sieve remaining amount of 7.6 mass %, a 160 µm-sieve remaining amount of 47.7 mass %, and a 45 µm-sieve remaining amount of 97.1 mass %. The polyethylene container including therein the raw material powder (901 g) was tightly closed and then heated at 70° C. in a dryer for 210 minutes. During heating for 210 minutes, the polyethylene container was removed once from the dryer every 30 minutes. In each case, the polyethylene container was placed on a shaker, and the raw material powder was sufficiently mixed for one minute. Subsequently, the polyethylene container was placed in the dryer again. The sequential procedure was repeated. After the heat treatment, a smooth and dry, white powder having a water content of 13 mass % was yielded. The white powder was subjected to powder X-ray diffraction analysis. As shown in FIG. 1, only a diffraction peak attributed to basic zinc cyanurate was detected, and no diffraction peak attributed to cyanuric acid or zinc oxide contained in the raw material was detected. The produced white powder was observed under a transmission electron microscope. As a result, the microparticles forming the powder were found to have a longer axis of 60 to 1,000 nm, a shorter axis of 40 to 140 nm, and a ratio of longer axis to shorter axis of 5 to 8. After drying at 110° C., the produced white powder was found to have a specific surface area of 18 $m^2/g$. The white powder was found to have a particle size corresponding to a 1,000 µm-sieve remaining amount of 0 mass %, a 400 µm-sieve remaining amount of 1.0 mass %, a 160 µm-sieve remaining amount of 41.8 mass %, and a 45

μm-sieve remaining amount of 90.5 mass %. Subsequently, the white powder (850 g) was dried in a dryer at 110° C., to thereby reduce the water content to 0.6%. The thus-dried white powder was dispersed in pure water, to thereby prepare a 5 mass % slurry having a pH of 6.5. The pH of the 5 mass % slurry was adjusted to 10 by use of 1 mass % aqueous sodium hydroxide. While the pH was then lowered with 1 mass % aqueous hydrochloric acid, zeta potential was measured. The zeta potential was −19 mV at a pH of 9.5, −21 mV at a pH of 8.9, −26 mV at a pH of 6.9, −24 mV at a pH of 4.8, and −16 mV at a pH of 4.0. The product of the white powder dried at 110° C. (2 g) and pure water (38 g) were placed in a polyethylene container (capacity: 50 mL), and the container was tightly closed. The contents were subjected to a dispersion treatment for 5 minutes by means of an ultrasound cleaner (40 kHz) (W-222, product of Honda Electronics Co., Ltd.), to thereby prepare a 5 mass % slurry. No sedimentation was detected in the slurry. The particle size of the slurry was determined through a laser diffraction technique. As a result, the mean particle size was found to be 1.0 μm, and the maximum particle size 45.6 μm. The particles exhibit excellent dispersibility in water.

Example 2

A raw material powder having a zinc oxide/cyanuric acid mole ratio of 2.5 and a water content of 13 mass % was prepared through the same procedure as employed in Example 1, and a portion (28.8 g) of the powder was removed. The raw material powder was placed in a polyethylene container (capacity: 250 mL), and the container was tightly closed and then heated at 80° C. in a dryer for 150 minutes. During heating for 150 minutes, the polyethylene container was removed once from the dryer every 30 minutes. In each case, the polyethylene container was placed on a shaker, and the raw material powder was sufficiently mixed for one minute. Subsequently, the polyethylene container was placed in the dryer again. The sequential procedure was repeated. After the heat treatment, a smooth and dry, white powder having a water content of 13 mass % was yielded. The white powder was subjected to powder X-ray diffraction analysis. Similar to Example 1, only a diffraction peak attributed to basic zinc cyanurate was detected, and no diffraction peak attributed to cyanuric acid or zinc oxide contained in the raw material was detected. The produced white powder was observed under a transmission electron microscope. As a result, the microparticles forming the powder were found to have a longer axis of 60 to 1,000 nm, a shorter axis of 40 to 150 nm, and a ratio of longer axis to shorter axis of 5 to 8. After drying at 110° C., the produced white powder was found to have a specific surface area of 17 m²/g. The white powder was found to have a particle size corresponding to a 1,000 μm-sieve remaining amount of 0 mass %, a 400 μm-sieve remaining amount of 5.9 mass %, a 160 μm-sieve remaining amount of 87.7 mass %, and a 45 μm-sieve remaining amount of 93.1 mass %. The product of the white powder dried at 110° C. (2 g) and pure water (38 g) were placed in a polyethylene container (capacity: 50 mL), and the container was tightly closed. The contents were subjected to a dispersion treatment for 5 minutes by means of an ultrasound cleaner (40 kHz) (W-222, product of Honda Electronics Co., Ltd.), to thereby prepare a 5 mass % slurry. The particle size of the slurry was determined through a laser diffraction technique. As a result, the mean particle size was found to be 3.4 μm, and the maximum particle size 195.8 μm.

Example 3

A raw material powder having a zinc oxide/cyanuric acid mole ratio of 2.5 and a water content of 13 mass % was prepared through the same procedure as employed in Example 1, and a portion (28.8 g) of the powder was removed. The raw material powder was placed in a polyethylene container (capacity: 250 mL), and the container was tightly closed and then heated at 90° C. in a dryer for 150 minutes. During heating for 150 minutes, the polyethylene container was removed once from the dryer every 30 minutes. In each case, the polyethylene container was placed on a shaker, and the raw material powder was sufficiently mixed for one minute. Subsequently, the polyethylene container was placed in the dryer again. The sequential procedure was repeated. After the heat treatment, a smooth and dry, white powder having a water content of 13 mass % was yielded. The white powder was subjected to powder X-ray diffraction analysis. Similar to Example 1, only a diffraction peak attributed to basic zinc cyanurate was detected, and no diffraction peak attributed to cyanuric acid or zinc oxide contained in the raw material was detected. The produced white powder was observed under a transmission electron microscope. As a result, the microparticles forming the powder were found to have a longer axis of 100 to 1,000 nm, a shorter axis of 40 to 200 nm, and a ratio of longer axis to shorter axis of 5 to 8. After drying at 110° C., the produced white powder was found to have a specific surface area of 14 m²/g. The white powder was found to have a particle size corresponding to a 1,000 μm-sieve remaining amount of 0 mass %, a 400 μm-sieve remaining amount of 6.4 mass %, a 160 μm-sieve remaining amount of 67.9 mass %, and a 45 μm-sieve remaining amount of 98.5 mass %. The product of the white powder dried at 110° C. (2 g) and pure water (38 g) were placed in a polyethylene container (capacity: 50 mL), and the container was tightly closed. The contents were subjected to a dispersion treatment for 5 minutes by means of an ultrasound cleaner (40 kHz) (W-222, product of Honda Electronics Co., Ltd.), to thereby prepare a 5 mass % slurry. The particle size of the slurry was determined through a laser diffraction technique. As a result, the mean particle size was found to be 6.9 μm, and the maximum particle size 297.0 μm.

Example 4

Zinc oxide powder (15.0 g) of Example 1 (grade 2 zinc oxide, product of Sakai Chemical Industry Co., Ltd.) and cyanuric acid powder (10.0 g) of Example 1 (product of Nissan Chemical Industries, Ltd., water content: 5.1 mass %) were placed in a polyethylene container (capacity: 250 mL), and then pure water (2.2 g) was added to the container. The container was placed on a shaker, and the contents were mixed for 10 minutes. Through the procedure, 27.2 g of a raw material powder having a zinc oxide/cyanuric acid mole ratio of 2.5 and a water content of 10 mass % was prepared. The raw material powder was found to have a 1,000 μm-sieve remaining amount of 0 mass %, a 400 μm-sieve remaining amount of 4.6 mass %, a 160 μm-sieve remaining amount of 40.4 mass %, and a 45 μm-sieve remaining amount of 99.3 mass %. The polyethylene container including therein the raw material powder was tightly closed and then heated at 80° C. in a dryer for 150 minutes. During heating for 150 minutes, the polyethylene container was removed once from the dryer every 30 minutes. In each case, the polyethylene container was placed on a shaker, and the raw material powder was sufficiently mixed for one minute.

Subsequently, the polyethylene container was placed in the dryer again. The sequential procedure was repeated. After the heat treatment, a smooth and dry, white powder having a water content of 10% was yielded. The white powder was subjected to powder X-ray diffraction analysis. Similar to Example 1, only a diffraction peak attributed to basic zinc cyanurate was detected, and no diffraction peak attributed to cyanuric acid or zinc oxide contained in the raw material was detected. The produced white powder was observed under a transmission electron microscope. As a result, the microparticles forming the powder were found to have a longer axis of 60 to 1,000 nm, a shorter axis of 40 to 140 nm, and a ratio of longer axis to shorter axis of 5 to 8. After drying at 110° C., the produced white powder was found to have a specific surface area of 17 $m^2/g$. The white powder was found to have a particle size corresponding to a 1,000 μm-sieve remaining amount of 0 mass %, a 400 μm-sieve remaining amount of 5.2 mass %, a 160 μm-sieve remaining amount of 54.1 mass %, and a 45 μm-sieve remaining amount of 98.2 mass %. The product of the white powder dried at 110° C. (2 g) and pure water (38 g) were placed in a polyethylene container (capacity: 50 mL), and the container was tightly closed. The contents were subjected to a dispersion treatment for 5 minutes by means of an ultrasound cleaner (40 kHz) (W-222, product of Honda Electronics Co., Ltd.), to thereby prepare a 5 mass % slurry. The particle size of the slurry was determined through a laser diffraction technique. As a result, the mean particle size was found to be 6.7 μm, and the maximum particle size 195.8 μm.

Example 5

A raw material powder having a zinc oxide/cyanuric acid mole ratio of 2.5 and a water content of 13 mass % was prepared through the same procedure as employed in Example 1, and a portion (28.8 g) of the powder was removed. The raw material powder was placed in a fluororesin container (capacity: 120 mL), and the container was tightly closed and then heated at 150° C. in a dryer for 50 minutes. After completion of heating, the container was cooled to room temperature, and the fluororesin container was removed from the dryer. The fluororesin container was placed on a shaker, and the raw material powder was mixed for one minute. Subsequently, the fluororesin container was placed again in the dryer at 150° C. for 50 minutes. The sequential procedure was repeated three times. Thus, the heat treatment at 150° C. was performed for 150 minutes in total. After the heat treatment, a smooth and dry, white powder having a water content of 13 mass % was yielded. The white powder was subjected to powder X-ray diffraction analysis. Similar to Example 1, only a diffraction peak attributed to basic zinc cyanurate was detected, and no diffraction peak attributed to cyanuric acid or zinc oxide contained in the raw material was detected. The produced white powder was observed under a transmission electron microscope. As a result, the microparticles forming the powder were found to have a longer axis of 100 to 800 nm, a shorter axis of 100 to 400 nm, and a ratio of longer axis to shorter axis of 2 to 5. After drying at 110° C., the produced white powder was found to have a specific surface area of 10 $m^2/g$. The white powder was found to have a particle size corresponding to a 1,000 μm-sieve remaining amount of 0 mass %, a 400 μm-sieve remaining amount of 9.0 mass %, a 160 μm-sieve remaining amount of 43.7 mass %, and a 45 μm-sieve remaining amount of 99.1 mass %. The product of the white powder dried at 110° C. (2 g) and pure water (38 g) were placed in a polyethylene container (capacity: 50 mL), and the container was tightly closed. The contents were subjected to a dispersion treatment for 5 minutes by means of an ultrasound cleaner (40 kHz) (W-222, product of Honda Electronics Co., Ltd.), to thereby prepare a 5 mass % slurry. The particle size of the slurry was determined through a laser diffraction technique. As a result, the mean particle size was found to be 11.7 μm, and the maximum particle size 129.1 μm.

Example 6

To cyanuric acid powder (320 g) of Example 1 (product of Nissan Chemical Industries, Ltd., water content: 5.1 mass %), pure water (123 g) was added. The cyanuric acid powder before mixing with water was dry and smooth. Zinc oxide powder (480 g) of Example 1 (grade 2 zinc oxide, product of Sakai Chemical Industry Co., Ltd.) was added to the cyanuric acid powder, to thereby prepare 923 g of a raw material powder having a zinc oxide/cyanuric acid mole ratio of 2.5 and a water content of 15 mass % was prepared. The raw material powder was found to have a 400 μm-sieve remaining amount of 7.3 mass %, a 160 μm-sieve remaining amount of 84.8 mass %, and a 45 μm-sieve remaining amount of 98.6 mass %. The raw material powder was added to a polyethylene container (capacity: 3 L). The container was tightly closed and then heated at 80° C. in a dryer for 270 minutes. During heating for 270 minutes, the polyethylene container was removed once from the dryer every 30 minutes. In each case, the polyethylene container was placed on a shaker, and the raw material powder was sufficiently mixed for one minute. Subsequently, the polyethylene container was placed in the dryer again. The sequential procedure was repeated. After the heat treatment, a smooth and dry, white powder having a water content of 15 mass % was yielded. The white powder was subjected to powder X-ray diffraction analysis. Similar to Example 1, only a diffraction peak attributed to basic zinc cyanurate was detected, and no diffraction peak attributed to cyanuric acid or zinc oxide contained in the raw material was detected. The produced white powder was observed under a transmission electron microscope. As a result, the microparticles forming the powder were found to have a longer axis of 60 to 1,000 nm, a shorter axis of 40 to 150 nm, and a ratio of longer axis to shorter axis of 5 to 8. After drying at 110° C., the produced white powder was found to have a specific surface area of 16 $m^2/g$. The white powder was found to have a particle size corresponding to a 1,000 μm-sieve remaining amount of 0 mass %, a 400 μm-sieve remaining amount of 3.3 mass %, a 160 μm-sieve remaining amount of 43.6 mass %, and a 45 μm-sieve remaining amount of 82.4 mass %. The product of the white powder dried at 110° C. (2 g) and pure water (38 g) were placed in a polyethylene container (capacity: 50 mL), and the container was tightly closed. The contents were subjected to a dispersion treatment for 5 minutes by means of an ultrasound cleaner (40 kHz) (W-222, product of Honda Electronics Co., Ltd.), to thereby prepare a 5 mass % slurry. The particle size of the slurry was determined through a laser diffraction technique. As a result, the mean particle size was found to be 10.8 μm, and the maximum particle size 159.0 μm.

Example 7

Zinc oxide powder (5.3 kg) of Example 1 (grade 2 zinc oxide, product of Sakai Chemical Industry Co., Ltd.) and cyanuric acid powder (3.4 kg) of Example 1 (product of Nissan Chemical Industries, Ltd., water content: 5.1 mass %) were placed in an open-type Roedige mixer (M-20: product of Chuo Kikoh), and the contents were preliminarily mixed for 3 minutes through rotation of the main shaft at 230 rpm. Subsequently, the cooling water passing through the jacket of the Roedige mixer was changed to steam (110° C.), to thereby elevate the temperature of the raw material powder to 80° C., and the pure water (1.5 kg) was sprayed into the mixer at a rate of 26 g/minutes over 58 minutes. At the moment, the raw material powder in the mixer was found to have a water content of 13 mass % and such a particle size that the 1,000 μm-sieve remaining amount was 0 mass %, the 400 μm-sieve remaining amount was 2.1 mass %, the 160 μm-sieve remaining amount was 64.8 mass %, and the 45 μm-sieve remaining amount was 95.0 mass %. Thereafter, the raw material powder was heated at 80° C. for 60 minutes, while the main shaft of the mixer was rotated at 230 rpm. The thus-treated powder was removed from the mixer. The recovered powder assumed a dry and smooth, white powder having a water content of 9 mass %. The white powder was subjected to powder X-ray diffraction analysis. Similar to Example 1, only a diffraction peak attributed to basic zinc cyanurate was detected, and no diffraction peak attributed to cyanuric acid or zinc oxide contained in the raw material was detected. The produced white powder was observed under a transmission electron microscope. As a result, the microparticles forming the powder were found to have a longer axis of 200 to 600 nm, a shorter axis of 30 to 100 nm, and a ratio of longer axis to shorter axis of 5 to 7. After drying at 110° C., the produced white powder was found to have a specific surface area of 15 m$^2$/g. The white powder was found to have a particle size corresponding to a 1,000 μm-sieve remaining amount of 0 mass %, a 400 μm-sieve remaining amount of 4.6 mass %, a 160 μm-sieve remaining amount of 39.3 mass %, and a 45 μm-sieve remaining amount of 95.7 mass %. The product of the white powder dried at 110° C. (2 g) and pure water (38 g) were placed in a polyethylene container (capacity: 50 mL), and the container was tightly closed. The contents were subjected to a dispersion treatment for 5 minutes by means of an ultrasound cleaner (40 kHz) (W-222, product of Honda Electronics Co., Ltd.), to thereby prepare a 5 mass % slurry. The particle size of the slurry was determined through a laser diffraction technique. As a result, the mean particle size was found to be 8.4 μm, and the maximum particle size 159.0 μm.

Example 8

Zinc oxide powder (15.0 g) of Example 1 (grade 2 zinc oxide, product of Sakai Chemical Industry Co., Ltd.) and cyanuric acid powder (10.0 g) of Example 1 (product of Nissan Chemical Industries, Ltd., water content: 5.1 mass %) were placed in a polyethylene container (capacity: 250 mL), and then pure water (1.3 g) was added to the container. The container was placed on a shaker, and the contents were mixed for 10 minutes. Through the procedure, 26.3 g of a raw material powder having a zinc oxide/cyanuric acid mole ratio of 2.5 and a water content of 7 mass % was prepared. The raw material powder was found to have a 1,000 μm-sieve remaining amount of 0 mass %, a 400 μm-sieve remaining amount of 3.0 mass %, a 160 μm-sieve remaining amount of 45.6 mass %, and a 45 μm-sieve remaining amount of 98.0 mass %. The polyethylene container including therein the raw material powder was tightly closed and then heated at 90° C. in a dryer for 150 minutes. During heating for 150 minutes, the polyethylene container was removed once from the dryer every 30 minutes. In each case, the polyethylene container was placed on a shaker, and the raw material powder was sufficiently mixed for one minute. Subsequently, the polyethylene container was placed in the dryer again. The sequential procedure was repeated. After the heat treatment, a smooth and dry, white powder having a water content of 7 mass % was yielded. The white powder was subjected to powder X-ray diffraction analysis. As a result, a diffraction peak attributed to basic zinc cyanurate was detected, and weak diffraction peaks attributed to cyanuric acid and zinc oxide contained in the raw material were also detected. The white powder was found to have a particle size corresponding to a 400 μm-sieve remaining amount of 2.0 mass %, a 160 μm-sieve remaining amount of 31.8 mass %, and a 45 μm-sieve remaining amount of 90.0 mass %.

Example 9

A raw material powder having a zinc oxide/cyanuric acid mole ratio of 2.5 and a water content of 13 mass % was prepared through the same procedure as employed in Example 1, and a portion (28.8 g) of the powder was removed. The raw material powder was placed in a polyethylene container (capacity: 250 mL), and the container was tightly closed and then heated at 40° C. in a dryer for 300 minutes. During heating for 300 minutes, the polyethylene container was removed once from the dryer every 30 minutes. In each case, the polyethylene container was placed on a shaker, and the raw material powder was sufficiently mixed for one minute. Subsequently, the polyethylene container was placed in the dryer again. The sequential procedure was repeated. After the heat treatment, a smooth and dry, white powder having a water content of 13 mass % was yielded. The white powder was subjected to powder X-ray diffraction analysis. As a result, a diffraction peak attributed to basic zinc cyanurate was detected, and weak diffraction peaks attributed to cyanuric acid and zinc oxide contained in the raw material were also detected. The white powder was observed under a transmission electron microscope. As a result, the microparticles forming the powder were found to have a longer axis of 60 to 1,000 nm, a shorter axis of 40 to 150 nm, and a ratio of longer axis to shorter axis of 5 to 8. After drying at 110° C., the produced white powder was found to have a specific surface area of 17 m$^2$/g. The white powder was found to have a particle size corresponding to a 1,000 μm-sieve remaining amount of 0 mass %, a 400 μm-sieve remaining amount of 5.1 mass %, a 160 μm-sieve remaining amount of 46.6 mass %, and a 45 μm-sieve remaining amount of 95.5 mass %.

Example 10

Zinc oxide powder (12.8 g) of Example 1 (grade 2 zinc oxide, product of Sakai Chemical Industry Co., Ltd.) and cyanuric acid powder (10.5 g) of Example 1 (product of Nissan Chemical Industries, Ltd., water content: 5.1 mass %) were placed in a polyethylene container (capacity: 250 mL), and then pure water (3.0 g) was added to the container. The container was placed on a shaker, and the contents were mixed for 10 minutes. Through the procedure, 26.3 g of a raw material powder having a zinc oxide/cyanuric acid mole ratio of 2.0 and a water content of 13 mass % was prepared. The raw material powder was found to have a 1,000 μm-sieve remaining amount of 0 mass %, a 400 μm-sieve remaining amount of 9.8 mass %, a 160 μm-sieve remaining amount of 75.0 mass %, and a 45 μm-sieve remaining amount of 99.2 mass %. The polyethylene container including therein the raw material powder was tightly closed and then heated at 80° C. in a dryer for 150 minutes. During heating for 150 minutes, the polyethylene container was removed once from the dryer every 30 minutes. In each case, the polyethylene container was placed on a shaker, and the raw material powder was sufficiently mixed for one minute. Subsequently, the polyethylene container was placed in the dryer again. The sequential procedure was repeated. After the heat treatment, a smooth and dry, white powder having a water content of 13 mass % was yielded. The white powder was subjected to powder X-ray diffraction analysis. As a result, a diffraction peak attributed to basic zinc cyanurate was detected, and a weak diffraction peak attributed to cyanuric acid contained in the raw material was also detected. The white powder was found to have a particle size corresponding to a 1,000 μm-sieve remaining amount of 0 mass %, a 400 μm-sieve remaining amount of 5.8 mass %, a 160 μm-sieve remaining amount of 27.5 mass %, and a 45 μm-sieve remaining amount of 96.0 mass %.

Example 11

Zinc oxide powder (15.0 g) of Example 1 (grade 2 zinc oxide, product of Sakai Chemical Industry Co., Ltd.) and cyanuric acid powder (8.3 g) of Example 1 (product of Nissan Chemical Industries, Ltd., water content: 5.1 mass %) were placed in a polyethylene container (capacity: 250 mL), and then pure water (3.1 g) was added to the container. The container was placed on a shaker, and the contents were mixed for 10 minutes. Through the procedure, 26.4 g of a raw material powder having a zinc oxide/cyanuric acid mole ratio of 3.0 and a water content of 13 mass % was prepared. The raw material powder was found to have a 1,000 μm-sieve remaining amount of 0 mass %, a 400 μm-sieve remaining amount of 7.1 mass %, a 160 μm-sieve remaining amount of 80.7 mass %, and a 45 μm-sieve remaining amount of 99.8 mass %. The polyethylene container including therein the raw material powder was tightly closed and then heated at 80° C. in a dryer for 150 minutes. During heating for 150 minutes, the polyethylene container was removed once from the dryer every 30 minutes. In each case, the polyethylene container was placed on a shaker, and the raw material powder was sufficiently mixed for one minute. Subsequently, the polyethylene container was placed in the dryer again. The sequential procedure was repeated. After the heat treatment, a smooth and dry, white powder having a water content of 13 mass % was yielded. The white powder was subjected to powder X-ray diffraction analysis. As a result, a diffraction peak attributed to basic zinc cyanurate was detected, and another diffraction peak attributed to zinc oxide contained in the raw material was also detected. The white powder was found to have a particle size corresponding to a 1,000 μm-sieve remaining amount of 0 mass %, a 400 μm-sieve remaining amount of 5.6 mass %, a 160 μm-sieve remaining amount of 32.2 mass %, and a 45 μm-sieve remaining amount of 95.8 mass %.

Example 12

To a polyethylene container (capacity: 3 L), cyanuric acid powder (401 g) of Example 1 (product of Nissan Chemical Industries, Ltd., water content: 5.1 mass %) and pure water (130 g) were added. The container was tightly closed and placed on a shaker, and the contents were mixed for 5 minutes. The powder before mixing with water was dry and smooth. Then, zinc oxide powder (600 g) of Example 1 (grade 2 zinc oxide, product of Sakai Chemical Industry Co., Ltd.) was added to the cyanuric acid powder contained in the polyethylene container (capacity: 3 L). The container was tightly closed and placed on a shaker, and the contents were mixed for 30 minutes, to thereby prepare 1,131 g of a raw material powder having a zinc oxide/cyanuric acid mole ratio of 2.5 and a water content of 13 mass % was prepared. The raw material powder was found to have a 400 μm-sieve remaining amount of 5.0 mass %, a 160 μm-sieve remaining amount of 86.8 mass %, and a 45 μm-sieve remaining amount of 99.0 mass %. The raw material powder was added to a polyethylene container (capacity: 3 L). The container was tightly closed and then heated at 90° C. in a dryer for 150 minutes. During heating for 150 minutes, the polyethylene container was removed once from the dryer every 30 minutes. In each case, the polyethylene container was placed on a shaker, and the raw material powder was sufficiently mixed for one minute. Subsequently, the polyethylene container was placed in the dryer again. The sequential procedure was repeated. After the heat treatment, a smooth and dry, white powder having a water content of 11 mass % was yielded. The white powder was subjected to powder X-ray diffraction analysis. Similar to Example 1, only a diffraction peak attributed to basic zinc cyanurate was detected, and no diffraction peak attributed to cyanuric acid or zinc oxide contained in the raw material was detected. The produced white powder was observed under a transmission electron microscope. As a result, the microparticles forming the powder were found to have a longer axis of 80 to 1,200 nm, a shorter axis of 30 to 200 nm, and a ratio of longer axis to shorter axis of 5 to 8. After drying at 110° C., the produced white powder was found to have a specific surface area of 14 m$^2$/g. The white powder was found to have a particle size corresponding to a 1,000 μm-sieve remaining amount of 0 mass %, a 400 μm-sieve remaining amount of 9.1 mass %, a 160 μm-sieve remaining amount of 41.5 mass %, and a 45 μm-sieve remaining amount of 99.5 mass %. The product of the white powder dried at 110° C. (2 g) and pure water (38 g) were placed in a polyethylene container (capacity: 50 mL), and the container was tightly closed. The contents were subjected to a dispersion treatment for 5 minutes by means of an ultrasound cleaner (40 kHz) (W-222, product of Honda Electronics Co., Ltd.), to thereby prepare a 5 mass % slurry. No sedimentation was observed in the slurry. The particle size of the slurry was determined through a laser diffraction technique. As a result, the mean particle size was found to be 2.0 μm, and the maximum particle size 45.6 μm. Excellent dispersibility in water was observed.

Comparative Example 1

Zinc oxide powder (15.0 g) of Example 1 (grade 2 zinc oxide, product of Sakai Chemical Industry Co., Ltd.) and cyanuric acid powder (10.0 g) of Example 1 (product of Nissan Chemical Industries, Ltd., water content: 5.1 mass %) were placed in a polyethylene container (capacity: 250 mL), and then pure water (6.2 g) was added to the container. The container was placed on a shaker, and the contents were mixed for 10 minutes. Through the procedure, a mixture having a zinc oxide/cyanuric acid mole ratio of 2.5 and a water content of 20 mass % was prepared. The thus-obtained mixture assumed aggregates having a size of some millimeters to 1 cm. The 1,000 μm-sieve remaining amount was 100 mass %. The aggregated material was added to a polyethylene container (capacity: 250 mL). The container was tightly closed and then heated at 80° C. in a dryer for 150 minutes. During heating for 150 minutes, the polyethylene container was removed once from the dryer every 30 minutes. In each case, the polyethylene container was placed on a shaker, and the aggregated material was sufficiently shaken for one minute. Subsequently, the polyethylene container was placed in the dryer again. The sequential procedure was repeated. After the heat treatment, smooth and dry, white aggregates having a size of some millimeters to 1 cm were yielded. The aggregated material had a 1,000 μm-sieve remaining amount of 100 mass %. The white aggregates were pulverized by means of a mortar, and the obtained powder was subjected to powder X-ray diffraction analysis. As a result, a diffraction peak attributed to basic zinc cyanurate was detected, and diffraction peaks attributed to cyanuric acid and zinc oxide contained in the raw material were also detected.

Comparative Example 2

Zinc oxide powder (15.0 g) of Example 1 (grade 2 zinc oxide, product of Sakai Chemical Industry Co., Ltd.) and cyanuric acid powder (10.0 g) of Example 1 (product of Nissan Chemical Industries, Ltd., water content: 5.1 mass %) were placed in a polyethylene container (capacity: 250 mL), and then pure water (16.0 g) was added to the container. The container was placed on a shaker, and the contents were mixed for 10 minutes. Through the procedure, a mixture having a zinc oxide/cyanuric acid mole ratio of 2.5 and a water content of 40 mass % was prepared. The thus-obtained mixture assumed a wet cake having a diameter of 2 to 3 cm and a 1,000 μm-sieve remaining amount of 100 mass %. The wet cake was added to a polyethylene container (capacity: 250 mL). The container was tightly closed and then heated at 80° C. in a dryer for 150 minutes. During heating for 150 minutes, the polyethylene container was removed once from the dryer every 30 minutes. In each case, the polyethylene container was placed on a shaker, and the cake was sufficiently shaken for one minute. Subsequently, the polyethylene container was placed in the dryer again. The sequential procedure was repeated. After the heat treatment, a hard and wet, white cake having a diameter of 2 to 3 cm was yielded. The cake had a 1,000 μm-sieve remaining amount of 100 mass %. Then, the wet white cake was dried at 50° C. and pulverized by means of a mortar, and the obtained powder was subjected to powder X-ray diffraction analysis. As a result, a diffraction peak attributed to basic zinc cyanurate was detected, and diffraction peaks attributed to cyanuric acid and zinc oxide contained in the raw material were also detected.

Comparative Example 3

Zinc oxide powder (15.0 g) of Example 1 (grade 2 zinc oxide, product of Sakai Chemical Industry Co., Ltd.) and cyanuric acid powder (10.0 g) of Example 1 (product of Nissan Chemical Industries, Ltd., water content: 5.1 mass %) were placed in a polyethylene container (capacity: 250 mL), and then pure water (47.0 g) was added to the container. The container was placed on a shaker, and the contents were mixed for 10 minutes. Through the procedure, a mixture having a zinc oxide/cyanuric acid mole ratio of 2.5 and a water content of 66 mass % was prepared. The thus-obtained mixture assumed a white wet cake of a disk shape having a diameter of about 5 cm and a 1,000 μm-sieve remaining amount of 100 mass %. The white wet cake was added to a polyethylene container (capacity: 250 mL). The container was tightly closed and then heated at 80° C. in a dryer for 150 minutes. During heating for 150 minutes, the polyethylene container was removed once from the dryer every 30 minutes. In each case, the polyethylene container was placed on a shaker, and the cake was sufficiently shaken for one minute. Subsequently, the polyethylene container was placed in the dryer again. The sequential procedure was repeated. After the heat treatment, a hard and wet, white cake of a disk shape having a diameter of about 5 cm was yielded. The cake had a 1,000 μm-sieve remaining amount of 100 mass %. Then, the white, hard and wet cake was dried at 50° C. and pulverized by means of a mortar, and the obtained powder was subjected to powder X-ray diffraction analysis. As a result, a diffraction peak attributed to basic zinc cyanurate was detected, and diffraction peaks attributed to cyanuric acid and zinc oxide contained in the raw material were also detected.

Comparative Example 4

Zinc oxide powder (15.0 g) of Example 1 (grade 2 zinc oxide, product of Sakai Chemical Industry Co., Ltd.) and cyanuric acid powder (10.0 g) of Example 1 (product of Nissan Chemical Industries, Ltd., water content: 5.1 mass %) were placed in a polyethylene container (capacity: 250 mL), and then pure water (57.0 g) was added to the container. The container was placed on a shaker, and the contents were mixed for 10 minutes. Through the procedure, a mixture having a zinc oxide/cyanuric acid mole ratio of 2.5 and a water content of 70 mass % was prepared. The thus-prepared mixture assumed a paste having a viscosity of 90,000 mPa·s and a 1,000 μm-sieve remaining amount of 100 mass %. The paste was added to a polyethylene container (capacity: 250 mL). The container was tightly closed and then heated at 80° C. in a dryer for 150 minutes. During heating for 150 minutes, the polyethylene container was removed once from the dryer every 30 minutes. In each case, the polyethylene container was placed on a shaker, and the paste was sufficiently shaken for one minute. Subsequently, the polyethylene container was placed in the dryer again. The sequential procedure was repeated. After the heat treatment, a hard and wet, white cake of a disk shape having a diameter of about 5 cm was yielded. The cake had a 1,000 μm-sieve remaining amount of 100 mass %. Then, the white, hard and wet cake was dried at 50° C. and pulverized by means of a mortar, and the obtained powder was subjected to powder X-ray diffraction analysis. As a result, a diffraction peak attributed to basic zinc cyanurate was detected, and diffraction peaks attributed to cyanuric acid and zinc oxide contained in the raw material were also detected. The product of the white powder dried at 110° C. (2 g) and pure water (38 g) were placed in a polyethylene container (capacity: 50 mL), and the container was tightly closed. The contents were subjected to a dispersion treatment for 5 minutes by means of an ultrasound cleaner (40 kHz) (W-222, product of Honda Electronics Co., Ltd.), to thereby prepare a 5 mass % slurry. A large number of aggregates having a size of about 5 mm were sedimented in the slurry. The particle size of the slurry was determined through a laser diffraction technique. As a result, the mean particle size was found to be 325.6 μm, and the maximum particle size 500 μm or greater, which was greater than the measurable limit.

Comparative Example 5

Zinc oxide powder (15.0 g) of Example 1 (grade 2 zinc oxide, product of Sakai Chemical Industry Co., Ltd.) and cyanuric acid powder (10.0 g) of Example 1 (product of Nissan Chemical Industries, Ltd., water content: 5.1 mass %) were placed in a polyethylene container (capacity: 250 mL), and then pure water (98.5 g) was added to the container. The container was placed on a shaker, and the contents were mixed for 10 minutes. Through the procedure, a mixture having a zinc oxide/cyanuric acid mole ratio of 2.5 and a water content of 80 mass % was prepared. The thus-prepared mixture assumed a high-viscosity slurry having a viscosity of 500 mPa·s. The slurry was found to have a 1,000 μm-sieve remaining amount of 97.1 mass %, a 400 μm-sieve remaining amount of 97.9 mass %, a 160 μm-sieve remaining amount of 99.2 mass %, and a 175 μm-sieve remaining amount of 100 mass %. The high-viscosity slurry was added to a polyethylene container (capacity: 250 mL). The container was tightly closed and then heated at 80° C. in a dryer for 150 minutes. During heating for 150 minutes, the polyethylene container was removed once from the dryer every 30 minutes. In each case, the polyethylene container was placed on a shaker, and the slurry was sufficiently shaken for one minute. Subsequently, the polyethylene container was placed in the dryer again. The sequential procedure was repeated. After the heat treatment, a white paste having a viscosity of 100,000 mPa·s or greater was yielded. The paste had a 1,000 μm-sieve remaining amount of 100 mass %. Then, the white paste was dried at 50° C. and pulverized by means of a mortar, and the obtained powder was subjected to powder X-ray diffraction analysis. As a result, only a diffraction peak attributed to basic zinc cyanurate was detected, and no diffraction peak attributed to cyanuric acid or zinc oxide contained in the raw material was detected. The product of the white powder dried at 110° C. (2 g) and pure water (38 g) were placed in a polyethylene container (capacity: 50 mL), and the container was tightly closed. The contents were subjected to a dispersion treatment for 5 minutes by means of an ultrasound cleaner (40 kHz) (W-222, product of Honda Electronics Co., Ltd.), to thereby prepare a 5 mass % slurry. A large number of aggregates having a size of about 5 mm were sedimented in the slurry. The particle size of the slurry was determined through a laser diffraction technique. As a result, the mean particle size was found to be 300.8 μm, and the maximum particle size 500 μm or greater, which was greater than the measurable limit.

Assessment of Rust Prevention

A coating paint for evaluation of rust prevention performance (200 g) was prepared in accordance with JIS-K5674. Specifically, Phthalit (registered trademark) Varnish (clear coating: product of Kansai Paint Co., Ltd. (96 g), DISPERBYK-103 (product of BYK Chemie) serving as a dispersant (4 g), barium sulfate (reagent grade) serving as an extender pigment (80 g), and the product of basic zinc cyanurate powder dried at 110° C. (Example 7) (20 g) were added to a 500-mL glass jar, and the contents were mixed by means of a high-speed agitator (Disper). The mixture was dispersed by means of a homogenizer at 20,000 rpm for 5 minutes. Also, a comparative coating paint (180 g) was prepared in accordance with JIS-K5674. Specifically, Phthalit (registered trademark) Varnish (clear coating: product of Kansai Paint Co., Ltd. (96 g), DISPERBYK-103 (product of BYK Chemie) serving as a dispersant (4 g), and barium sulfate (reagent grade) serving as an extender (80 g) were added to a 500-mL glass jar, and the contents were mixed and dispersed by means of a high-speed agitator (Disper). The mixture was dispersed by means of a homogenizer at 20,000 rpm for 5 minutes.

Onto a steel sheet SPCC-SS (150 mm×70 mm×0.8 mm) finished with water-proof abrasive paper, the above-prepared coating paint (1.0 g) for evaluation of rust prevention performance was applied through brush coating and dried at 40° C. for 2 hours. The same coating paint (1.0 g) was further applied through brush coating and dried at 40° C. for 2 hours. Through this procedure, three steel sheets provided with the coating film were prepared. The coating surface of each steel sheet was scratched with a knife so as to be provided with a cross pattern, and the back surface of the sheet was protected with a protective seal, to thereby provide a test piece. Three test pieces for evaluation and those for comparison were placed in a complex cycle tester (product of Suga Test Instruments Co., Ltd.). In the test, 5-mass % saline was sprayed at 30° C. to each test piece for 5 minutes, and the test piece was subjected to a wet test at 30° C. and a humidity of 95% for 1.5 hours. Subsequently, the test piece was dried at 50° C. for 2 hours though hot air blow and then at 30° C. for 2 hours in the similar manner (1 cycle: 6 hours).

TABLE 1

| Formed powder | | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|
| 1000 μm-sieve | % | 0 | 0 | 0 | 0 | 0 | 0 | 0 | 0 | 0 |
| 400 μm-sieve | % | 1.0 | 5.9 | 6.4 | 5.2 | 9.0 | 3.3 | 4.6 | 2.0 | 5.1 |
| 160 μm-sieve | % | 41.8 | 87.7 | 67.9 | 54.1 | 43.7 | 43.6 | 39.3 | 31.8 | 46.6 |
| 45 μm-sieve | % | 90.5 | 93.1 | 98.5 | 98.2 | 99.1 | 82.4 | 95.7 | 90.0 | 95.5 |
| Cryst. phase | | BCZ | BCZ | BCZ | BCZ | BCZ | BCZ | BCZ | BCZ + ZnO + CA | BCZ + ZnO + CA |
| TEM/longer axis | nm | 60-1000 | 60-1000 | 60-1000 | 60-1000 | 100-800 | 60-1000 | 200-600 | — | 60-1000 |
| TEM/shorter axis | nm | 40-140 | 40-150 | 40-200 | 40-140 | 100-400 | 40-150 | 30-100 | — | 40-150 |
| Axis ratio | | 5-8 | 5-8 | 5-8 | 5-8 | 2-5 | 5-8 | 5-7 | — | 5-8 |

| Formed powder | | Ex. 10 | Ex. 11 | Ex. 12 | Comp. 1 | Comp. 2 | Comp. 3 | Comp. 4 | Comp. 5 |
|---|---|---|---|---|---|---|---|---|---|
| 1000 μm-sieve | % | 0 | 0 | 0 | 100 | 100 | 100 | 100 | 100 |
| 400 μm-sieve | % | 5.8 | 5.6 | 9.1 | — | — | — | — | — |
| 160 μm-sieve | % | 27.5 | 32.2 | 41.5 | — | — | — | — | — |
| 45 μm-sieve | % | 96.0 | 95.8 | 99.5 | — | — | — | — | — |
| Cryst. phase | | BCZ + CA | BCZ + ZnO | BCZ | BCZ + ZnO + CA | BCZ + ZnO + CA | BCZ + ZnO + CA | BCZ + ZnO + CA | BCZ |
| TEM/longer axis | nm | — | — | 80-1200 | — | — | — | — | — |
| TEM/shorter axis | nm | — | — | 30-200 | — | — | — | — | — |
| Axis ratio | | — | — | 5-8 | — | — | — | — | — |

BCZ: basic zinc cyanurate,
ZnO: zinc oxide,
CA: cyanuric acid

The cycle was performed 36 times. Then, the test piece was removed from the tester and washed with tap water, followed by drying at 25° C. Then, the blister width of the test piece was measured. As a result, test pieces coated with a coating paint for evaluation of rust prevention performance exhibited a maximum blister width of 2 mm, which is smaller by 3 mm than the JIS standard width. Thus, no swelling was found to occur, and excellent rust prevention performance was confirmed. In contrast, test pieces coated with a comparative coating paint exhibited a maximum blister width of 10 mm.

INDUSTRRIAL APPLICABILITY

According to the present invention, a highly rust-preventive basic zinc cyanurate powder can be produced at high efficiency and at low cost. The powder can eliminate a pulverization step. By use of the thus-produced basic zinc cyanurate powder, a highly rust-preventive and non-hazardous (Pb- and Cr-free) rust-preventive coating paint can be produced.

The invention claimed is:

1. A method for producing a basic zinc cyanurate powder having a 1,000 μm-sieve remaining amount less than 1 mass %, the 1,000 μm-sieve remaining amount being determined by placing a sample into a sieve having a mesh size of 1,000 μm, and sieving the sample, the 1,000 μm-sieve remaining amount being the amount that remains in the sieve having the mesh size of 1,000 μm, wherein the method comprises:
   forming a powder-form mixture by mixing zinc oxide, cyanuric acid, and water at a ratio by mole of zinc oxide to cyanuric acid of 2 to 3, and at a water content of 9 to 18 mass %; and
   heating the powder-form mixture at 30 to 300° C. in a closed or unclosed state.

2. A method according to claim 1 for producing the basic zinc cyanurate powder having a 1,000 μm-sieve remaining amount less than 1 mass %, wherein the powder-form mixture has a 1,000 μm-sieve remaining amount less than 1 mass % and a 400 μm-sieve remaining amount less than 10 mass %.

3. A method according to claim 1 for producing the basic zinc cyanurate powder having a 1,000 μm-sieve remaining amount less than 1 mass %, wherein the basic zinc cyanurate powder has a primary particle longer axis of 50 to 2,000 nm and a primary particle shorter axis of 20 to 300 nm, as obtained through observation of the primary particles under a transmission electron microscope.

4. A method according to claim 2 for producing the basic zinc cyanurate powder having a 1,000 μm-sieve remaining amount less than 1 mass %, wherein the basic zinc cyanurate powder has a primary particle longer axis of 50 to 2,000 nm and a primary particle shorter axis of 20 to 300 nm, as obtained through observation of the primary particles under a transmission electron microscope.

5. A method according to claim 3 for producing the basic zinc cyanurate powder having a 1,000 μm-sieve remaining amount less than 1 mass %, wherein the ratio of the longer axis of the zinc cyanurate particle to the shorter axis thereof is 2 to 10.

6. A method according to claim 4 for producing the basic zinc cyanurate powder having a 1,000 μm-sieve remaining amount less than 1 mass %, wherein the ratio of the longer axis of the zinc cyanurate particle to the shorter axis thereof is 2 to 10.

7. A method according to claim 1 for producing the basic zinc cyanurate powder having a 1,000 μm-sieve remaining amount less than 1 mass %, wherein heating is performed by means of a powder mixer having mixing means and heating means.

8. A method according to claim 2 for producing the basic zinc cyanurate powder having a 1,000 μm-sieve remaining amount less than 1 mass %, wherein heating is performed by means of a powder mixer having mixing means and heating means.

9. A method according to claim 3 for producing the basic zinc cyanurate powder having a 1,000 μm-sieve remaining amount less than 1 mass %, wherein heating is performed by means of a powder mixer having mixing means and heating means.

10. A method according to claim 4 for producing the basic zinc cyanurate powder having a 1,000 μm-sieve remaining amount less than 1 mass %, wherein heating is performed by means of a powder mixer having mixing means and heating means.

11. A method according to claim 5 for producing the basic zinc cyanurate powder having a 1,000 μm-sieve remaining amount less than 1 mass %, wherein heating is performed by means of a powder mixer having mixing means and heating means.

12. A method according to claim 6 for producing a basic zinc cyanurate powder having a 1,000 μm-sieve remaining amount less than 1 mass %, the wherein heating is performed by means of a powder mixer having mixing means and heating means.

13. A method for producing a rust-preventive pigment composition, the method comprising:
   forming a powder-form mixture by mixing zinc oxide, cyanuric acid, and water at a ratio by mole of zinc oxide to cyanuric acid of 2 to 3, and at a water content of 9 to 18 mass %;
   heating the powder-form mixture at 50 to 300° C. in a closed or unclosed state to produce a basic zinc cyanurate powder having a 1,000 μm-sieve remaining amount less than 1 mass %, the 1,000 μm-sieve remaining amount being determined by placing a sample into a sieve having a mesh size of 1,000 μm, and sieving the sample, the 1,000 μm-sieve remaining amount being the amount that remains in the sieve having a mesh size of 1,000 μm; and
   mixing the basic zinc cyanurate powder having a 1,000 μm-sieve remaining amount less than 1 mass % with a binder component and a diluent.

14. A method according to claim 13 for producing a rust-preventive pigment composition, wherein the binder is an oily binder or a synthetic resin binder.

15. A method according to claim 13 for producing a rust-preventive pigment composition, wherein the diluent is at least one species selected from the group consisting of water, turpentine, mineral spirit, toluene, xylene, methyl ethyl ketone, methyl isobutyl ketone, cellosolve acetate, ethanol, butanol, isopropyl alcohol, cyclohexane, ethyl acetate, and butyl acetate.

* * * * *